United States Patent
Wang

(10) Patent No.: US 9,655,576 B2
(45) Date of Patent: May 23, 2017

(54) X-RAY PHASE-SHIFT CONTRAST IMAGING METHOD AND SYSTEM THEREOF

(71) Applicant: GAMC Biotech Development Co., LTD., New Taipei (TW)

(72) Inventor: Chia-Gee Wang, New York, NY (US)

(73) Assignee: NanoRay Biotech Co., Ltd., New Taipei (TW)

( * ) Notice: Subject to any disclaimer, the term of this patent is extended or adjusted under 35 U.S.C. 154(b) by 55 days.

(21) Appl. No.: 13/671,567

(22) Filed: Nov. 8, 2012

(65) Prior Publication Data

US 2013/0129038 A1 May 23, 2013

Related U.S. Application Data

(60) Provisional application No. 61/557,351, filed on Nov. 8, 2011.

(30) Foreign Application Priority Data

Nov. 7, 2012 (TW) .............................. 101141445 A

(51) Int. Cl.
*A61B 6/00* (2006.01)
*A61B 6/02* (2006.01)

(52) U.S. Cl.
CPC .............. *A61B 6/484* (2013.01); *A61B 6/022* (2013.01); *A61B 6/482* (2013.01); *A61B 6/502* (2013.01); *A61B 6/4007* (2013.01)

(58) Field of Classification Search
CPC ......... A61B 6/022; A61B 6/482; A61B 6/484; A61B 6/502; A61B 6/4007

(Continued)

(56) References Cited

U.S. PATENT DOCUMENTS 7,180,981 B2 2/2007 Wang
7,430,276 B2 9/2008 Wang et al.
(Continued)

FOREIGN PATENT DOCUMENTS

JP 2007-097610 4/2007
JP 2009-150875 7/2009
(Continued)

OTHER PUBLICATIONS

Yokhin, B.,Wide angle geometry EDXRF spectrometers with secondary target and direct excitation modes, 2000, International Centre for Diffraction Data: Advances in X-ray Analysis, vol. 12, p. 11-15.*

(Continued)

*Primary Examiner* — Glen Kao
(74) *Attorney, Agent, or Firm* — Jianq Chyun IP Office

(57) ABSTRACT

An X-ray phase-shift contrast imaging method and the system thereof are provided. The X-ray phase-shift contrast imaging method utilizes characteristic X-rays of high throughput irradiating at the target from different positions or with different focal positions so as to form different X-ray images. The X-ray images are compared to define the voxels and combined to obtain a 3-D X-ray image. By using X-ray phase-shift contrast for imaging the soft tissue, the level of the image contrast may be enhanced several orders of magnitude and the linear energy transfer of the high energy photon beam is greatly reduced. Hence, the radiation dose absorbed by the tissue may be greatly reduced.

20 Claims, 9 Drawing Sheets

(58) Field of Classification Search
USPC .......... 378/9, 37, 41, 55, 62, 98.8, 121, 124, 378/140, 143, 197
See application file for complete search history.

(56) References Cited

U.S. PATENT DOCUMENTS

| | | |
|---|---|---|
| 7,826,592 B2 | 11/2010 | Jaffray et al. |
| 2005/0123097 A1* | 6/2005 | Wang .......................... 378/143 |
| 2007/0274435 A1* | 11/2007 | Ning et al. ........................ 378/4 |
| 2009/0238334 A1* | 9/2009 | Brahme et al. ................. 378/41 |
| 2011/0282181 A1 | 11/2011 | Wang et al. |
| 2012/0265050 A1 | 10/2012 | Wang |

FOREIGN PATENT DOCUMENTS

| | | |
|---|---|---|
| JP | 2012-024339 | 2/2012 |
| TW | 201209847 | 3/2012 |

OTHER PUBLICATIONS

"Office Action of Taiwan Counterpart Application", issued on Mar. 19, 2014, p. 1-p. 4.
"Office Action of PCT Counterpart Application", issued on Apr. 4, 2014, p. 1-p. 16.
"Office Action of Japan Counterpart Application", issued on Jul. 5, 2016, p. 1-p. 5.

* cited by examiner (a)

(b)

(a)

(b)

X-RAY PHASE-SHIFT CONTRAST IMAGING METHOD AND SYSTEM THEREOF

CROSS-REFERENCE TO RELATED APPLICATION

This application claims the priority benefits of U.S. provisional application Ser. No. 61/557,351, filed on Nov. 8, 2011 and Taiwan application serial no. 101141445, filed on Nov. 7, 2012. The entirety of each of the above-mentioned patent applications is hereby incorporated by reference herein and made a part of this specification.

BACKGROUND OF THE INVENTION

Field of the Invention

The present invention relates to an imaging method. More particularly, the present invention relates to an X-ray phase-shift contrast imaging method and the system thereof.

Description of Related Art

Mammography employs low-dosage X-ray (about 0.7 mili-sievert) to examine the human breasts, mainly woman's breasts, which is able to detect various breast diseases, such as cancers and cysts. Mammography has been an important diagnostic instrument responsible for the early detection of breast cancer and consequently the much enhanced survival rate for the patients diagnosed with breast cancer.

In mammography, like X-ray examinations, the ionized radiation is applied to the human body and the accumulation of the radiation has to be considered. The relatively high ionization dose of mammography may initiate radiation-induced carcinoma. Also, for patents with thick and dense tissue that does not offer a clear image, high error rates in cancer diagnosis (at least 10% of false negative rate) greatly reduces the benefits of mammography. The dose problem makes the question of whether or not to use it, when to use it, and how often to use it a troublesome issue.

If mammography dose can be reduced dramatically, and also enhance image resolution, it would greatly improve the woman's healthcare in a highly cost-effective manner.

On the other hand, the global market for mammography equipments is pretty huge as up to 3300 units of equipments may be sold each year and the unit price of the digital mammography system is expensive. Hence, the demand for the mammography system of lower costs and high 3-D resolution is rather high.

SUMMARY OF THE INVENTION

The present invention related to an X-ray phase-shift contrast imaging method and the system thereof, which employs low dose radiation but offer high image contrast. Furthermore, compared with the conventional expensive mammography system, the production costs of the X-ray phase-shift contrast imaging system of this invention is significantly lowered by the simplified design thereof.

The present invention provides an X-ray phase-shift contrast imaging method. Firstly, at least an X-ray tube is provided and an X-ray beam is generated by the X-ray tube. The X-ray beam irradiates to a tissue in a first direction to obtain a first X-ray image and in a second direction to obtain a second X-ray image. The X-ray beam has a throughput ratio of characteristic X-rays and continuous X-rays is at least 5:1. The first X-ray image and the second X-ray image are received and compared by a two-dimensional detection array to define voxels, so as to obtain a three-dimensional X-ray image.

As embodied and broadly described herein, the X-ray tube includes a casing offering a vacuum environment, and anode, a cathode and a transmission yep target. The anode is disposed within an end window of the casing, while the cathode is disposed in the casing. The transmission type target is disposed on the anode and includes at least a foil. The cathode is suitable for emitting an electron beam along a path in the casing to strike onto the transmission type target to generate the X-ray beam passing through the end window.

The present invention also provides an X-ray phase-shift contrast imaging system, which is suitable for obtaining images of a tissue. The X-ray phase-shift contrast imaging system includes a two-dimensional image detection array and two X-ray tubes respectively located at a first position and a second position. The two X-ray tubes generate X-ray beams irradiating on the tissue respectively in a first direction to form a first X-ray image and in a second direction to form a second X-ray image. The first X-ray image and the second X-ray image are received by the two-dimensional image detection array. Each of the two X-ray tubes includes a transmission type target located on an anode and a cathode emitting an electron beam to bombard the transmission type target so as to generate the X-ray beams. The X-ray beam has a throughput ratio of characteristic X-rays and continuous X-rays is at least 5:1.

The present invention provides an X-ray phase-shift contrast imaging system suitable for obtaining images of a tissue. The X-ray phase-shift contrast imaging system includes a two-dimensional image detection array and a transmission X-ray tube for generating an X-ray beam. The X-ray beam is generated by the transmission X-ray tube located respectively at a first position and a second position to irradiate on the tissue respectively in a first direction to form a first X-ray image and in a second direction to form a second X-ray image. The first X-ray image and the second X-ray image are received by the two-dimensional image detection array. The transmission X-ray tube includes a transmission type target located on an anode and a cathode emitting an electron beam to bombard the transmission type target so as to generate the X-ray beams. The X-ray beam has a throughput ratio of characteristic X-rays and continuous X-rays is at least 5:1.

As embodied and broadly described herein, the X-ray beam may be a wide-angle conic X-ray beam. The characteristic X-rays may be monochromatic X-rays.

In order to make the aforementioned and other objects, features and advantages of the present invention comprehensible, embodiments accompanied with figures are described in detail below. It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

The present invention is described below in detail with reference to the accompanying drawings, and the embodiments of the present invention are shown in the accompanying drawings. However, the present invention can also be implemented in a plurality of different forms, so it should not be interpreted as being limited in the following embodiments. Actually, the following embodiments are intended to demonstrate and illustrate the present invention in a more detailed and completed way, and to fully convey the scope of the present invention to those of ordinary skill in the art. A brief estimate of the physics of the phase-shifted contrast is provided prior to the detailed disclosure. In the accompanying drawings, in order to be specific, the size and relative size of each layer and each region may be exaggeratedly depicted.

Figure 1:
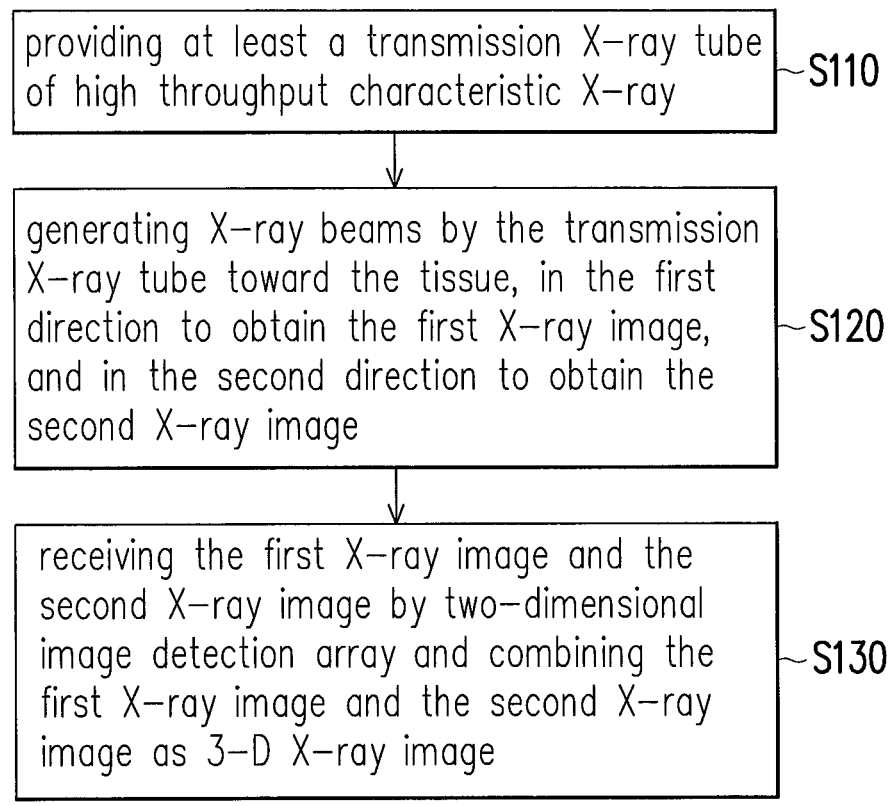
FIG. 1 is a flow chart showing the process steps of an X-ray phase-shift contrast imaging method according to an embodiment of this invention.
Figure 2:
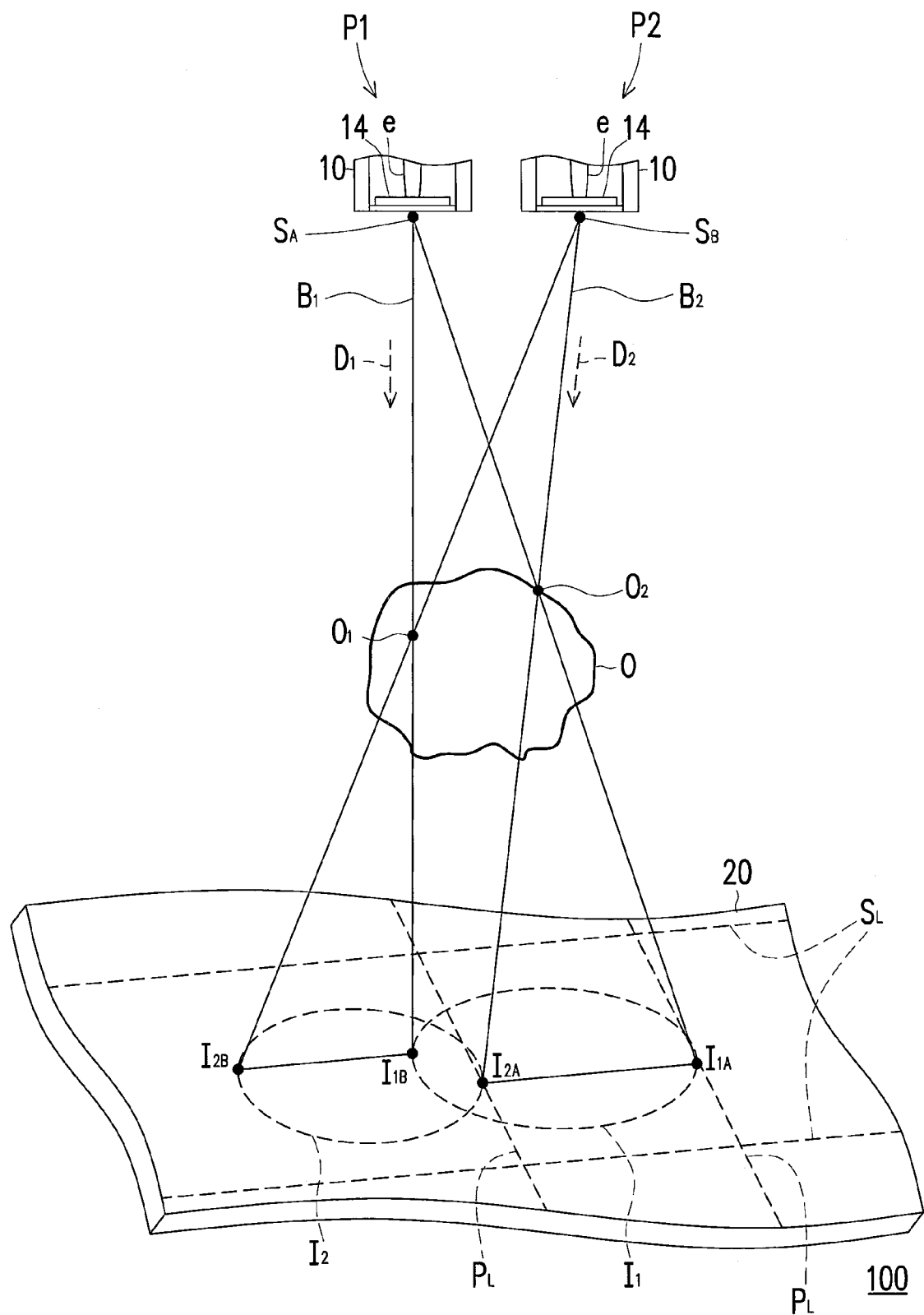
FIG. 2 is a schematic display of an X-ray phase-shift contrast imaging system for the X-ray phase-shift contrast imaging method according to an embodiment of this invention.

FIG. 1 is a flow chart showing the process steps of an X-ray phase-shift contrast imaging method according to an embodiment of this invention. FIG. 2 is a schematic display of an X-ray phase-shift contrast imaging system for the X-ray phase-shift contrast imaging method of the embodiment. Referring to FIGS. 1 & 2, the X-ray phase-shift contrast imaging method includes at least the following steps. At first, providing at least a transmission X-ray tube 10 of high throughput characteristic X-rays (Step S110). Later, the transmission wide-angle X-ray tube 10 generates X-ray beams $B_1$, $B_2$, where the wide-angle X-ray beam $B_1$ is irradiated at the tissue O in the first direction $D_1$ to obtain the first X-ray image $I_1$, and the wide-angle X-ray beam $B_2$ is irradiated at the tissue O in the second direction $D_2$ to obtain the second X-ray image $I_2$ (Step S120). Then, the first X-ray image $I_1$ and the second X-ray image $I_2$ are received and compared by a two-dimensional image detection array 20 to define the 3-D voxels by converting the pixels into the voxels, and the voxels are visualized as the 3-D X-ray image (Step S130).

In details, for the X-ray phase-shift contrast imaging system 100 of FIG. 2, the tissue O is placed between the two X-ray beam sources $S_A$, $S_B$ and a two-dimensional image detection array 20. In this embodiment, the X-ray beam sources $S_A$, $S_B$ are respectively located at the two positions $P_1$, $P_2$ and are provided by the same type of two transmission X-ray tubes 10. A metal tag T of a size of about 1 mm is placed on the tissue surface as a reference for calibrating the images. The X-ray beam sources $S_A$, $S_B$ emit two X-ray beams $B_1$, $B_2$, and the X-ray beams $B_1$, $B_2$ are respectively in the first direction $D_1$ and the second direction $D_2$ irradiated at the tissue O, to generate the partially overlapped first X-ray image $I_1$ and second X-ray image $I_2$. Later, the two-dimensional image detection array 20 is used to receive the first X-ray image $I_1$ and the second X-ray image $I_2$. In this embodiment, the X-ray beams $B_1$, $B_2$ may be irradiated at the tissue O in sequence or at the same time.

Because the distance between the two-dimensional image detection array 20 and the metal tag T is different to the distance between the two-dimensional image detection array 20 and the target region $O_1$, the magnification factor at the pixels $I_{1A}$, $I_{1B}$ is different to the magnification factor at the pixels $I_{2A}$, $I_{2B}$. If the pixels $I_{1A}$, $I_{1B}$, $I_{2A}$, $I_{2B}$ at the two-dimensional image detection array 20 may be superimposed by using the linear shift as a function of the distance between the two positions $P_1$, $P_2$, the two-dimensional image detection array 20 can send out the two-dimensional images, together with the magnification factor of the target region $O_1$. In other words, by way of the two-dimensional multi-collinearity of the pixels $I_{1A}$, $I_{1B}$, $I_{2A}$, $I_{2B}$, the 3-D voxel points are sent out to form the 3-D image.

For example, referring to FIG. 2, during the image processing, the pixels $I_{1A}$ and $I_{2A}$ generated through the metal tag T are respectively selected from the first X-ray image $I_1$ and the second X-ray image $I_2$ on the two-dimensional image detection array 20, and a connection line of $I_{1A}$-$I_{2A}$ is established. Later, a plurality of pixel lines $P_L$ orthogonal to the connection line of $I_{1A}$-$I_{2A}$ is established on the two-dimensional image detection array 20 and all the pixels are set with the corresponding line coordinates. In addition, a plurality of scanning lines $S_L$ parallel to the connection line of $I_{1A}$-$I_{2A}$ is established on the two-dimensional image detection array 20.

In FIG. 2, when the scanning lines $S_L$ cross with the pixel lines $P_L$, the pixel data are compared with the scanning lines $S_L$, so as to identify all the image pairs similar to the connection line of $I_{1A}$-$I_{2A}$. For example, the pixels $I_{1B}$ and $I_{2B}$ and the connection line of $I_{1B}$-$I_{2B}$ in the first X-ray image $I_1$ and the second X-ray image $I_2$ generated through the target region $O_1$ of the tissue O can be identified. Taking advantages of the above mentioned image pairs (including the connection lines of $I_{1A}$-$I_{2A}$ and $I_{1B}$-$I_{2B}$), the 3-D position of the target region $O_1$ in the tissue O is provided, and this position may be defined as a voxel (point) by the calculator during the image processing. As the 3-D voxel positions of the other regions of the tissue O and the corresponding voxels are identified one-by-one, the 3-D image structure of the whole tissue O can be decided.

The scope of this invention is limited to the above embodiment(s), and the two-dimensional pixel image detection array 20 may employ other suitable calculations or processing methods to visualize the 3-D X-ray image(s).

Figure 3:
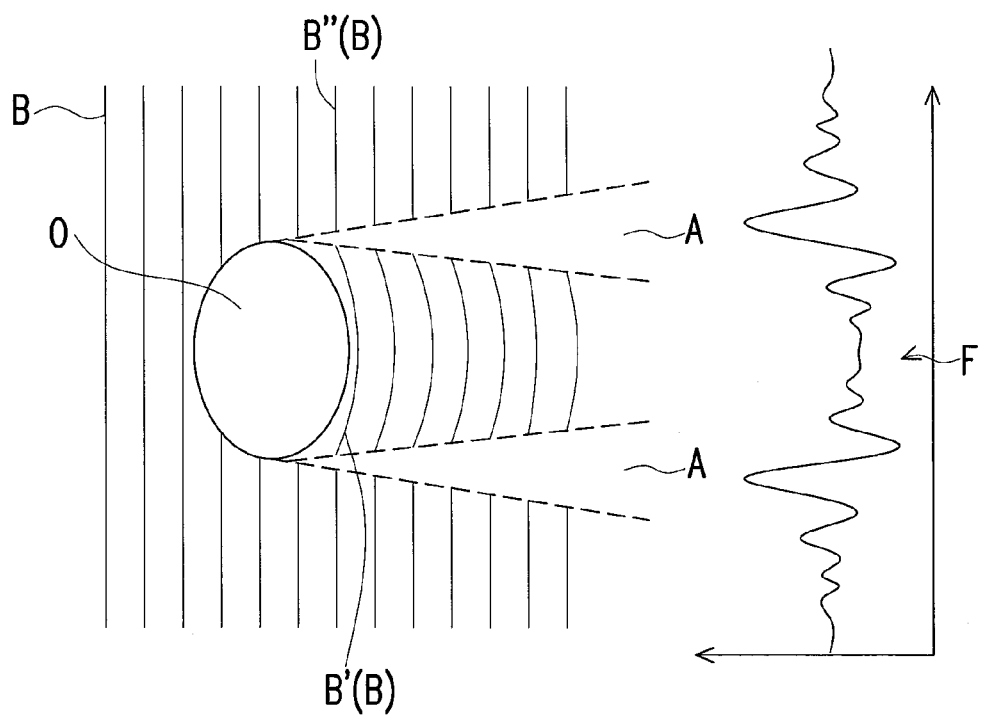
FIG. 3 illustrates the general mechanism for the generation of the X-ray images.

According to the embodiment as shown in FIG. 1, for the X-ray phase-shift contrast imaging method, the first X-ray image $I_1$ and the second X-ray image $I_2$ are phase-shift contrast imaging data. More detailed descriptions about the phase-shift contrast imaging method will be explained as follows. FIG. 3 illustrates the general mechanism of the generation of the X-ray images. Referring to FIG. 3, the phase-shift contrast imaging method exploits differences in the refractive index of different materials by X-ray. When the coherent X-ray beam B is irradiated at the tissue O, because the region of the tissue O and the region surrounding the tissue O have different index of refraction toward the X-ray beam B, if there is phase shift caused by different light velocities between the X-ray beam B' passing through the tissue O and the X-ray beam B" passing through the tissues surrounding the tissue O. Owing to the difference in phase shifts, the X-ray beam B' and the X-ray beam B" are interfered with each other in the overlapped region A, thus forming the X-ray interference intensity pattern F. In other words, as described in the embodiment shown by FIG. 2, the X-ray beams $B_1$, $B_2$ are irradiated at the tissue O in respectively the first direction $D_1$ and the second direction $D_2$. As the various regions of the tissue O have different impacts on the light velocity of X-ray, the first X-ray image $I_1$ and the second X-ray image $I_2$ along with the interference information are generated.

Comparing with the imaging method using the differences in the X-ray absorption amounts among the tissues, the phase-shift contrast imaging method could potentially provide much higher image-contrast. Especially under the circumstances that the tissues have little differences in the X-ray absorption amounts such as the soft tissues in the breast, the phase-shift contrast imaging method could acquire much clearer X-ray images. For X-ray phase-shift contrast imaging method, the tissue O may be a soft tissue, i.e. the tissue consisting of low Z elements. For example, the breasts may be an example of the soft tissue. The physics of using phase-shift contrast is outlined as follows.

Conventional mammography cannot make use phase-shifted image contrast. In a conventional mammography, approximately 94% of the X-ray effluence is absorbed by the breast tissue, only remaining 6% reaches the imaging detector. A change of tissue absorption of 2% by cist, tumor, or tubular tissues from the fat, for example, will decrease X-ray photons reaching the detector from 6% to 4%, thus forming the detector's imaging contrast between 6% and 4% of photons transmitted through the tissues. If a tissue would absorb a high energy photon beam at 50%, implying that the detector would receive the remaining 50% for fat or 49% for tumor, such a low difference would yield no clear tumor image what so ever. In other words, the conventional mammography must "fry" the breast tissue in order to allow a small leftover effluence for imaging. Conventional mammography tube uses ≅100 mAs (milliamp-second) per view, and in a 0.5 second exposure, the X-ray tube current is ≅200 mA, using a tube voltage of 22-28 kV, whose thermal load to the X-ray tube target is approximately 5 kilo Watts, implying that the X-ray tube must use a rotational anode disk in order to spread the thermal load to a large target area. It implies also that the spot size of the e-beam target on the anode disk cannot be focused at much smaller than 500 μm.

Forming a phase-shifted imaging contrast from a transmission tube, both the X-ray generating layer thickness and the detector pixel size must be kept at a level necessary for certain coherence lengths in order for the photon beam to interfere with sufficient coherency, although photons at different wave lengths (poly-chromatic) are not nearly as important as one might suspect (to be considered later). X-ray beam spot size, which is typically the e-beam target size of the anode, must be sufficiently large in order to spread the thermal load, and this is in fact less of an issue in the transmission X-ray tubes than those in the conventional mammography tubes because of their difference in power level in the respective image formations.

For a transmission mammography tube, the spectrum of mostly characteristic line-emissions is almost independent to variations of the e-beam voltage so that the tube voltage can be raised to 80-100 kV instead of limiting at a range of 20-28 kV, and this is done without using external filter to reach a desired spectrum, nor having the total beam brightness reduced. A higher tube voltage enhances the tube effluence by kVp to the 2.1th power, or an increase in efficiency by a factor of 3 from the conventional mammography tubes. The transmission tube provides also a broad angle with uniform emissions in beam delivery so that the detector can be placed nearer to the X-ray focal spot without missing any coverage of the tissue overall and this gains the detector photon counts by another factor of 2. Most important in the phase-shifted contrast is the contrast formation in the phase-shifted interference, it could be enhanced from the usual difference in absorptions by several orders of magnitude, as a result, the X-ray photons can be selected to allow the breast tissue to share the X-ray beam equally, at 50/50 with the detector, for example, instead of 94/6 as mentioned above, and this order of magnitude increase of the photon fraction registered by the same detector counts implying that an order of magnitude reduction for the total X-ray tube output. Combining the above mentioned evaluations, the power needed by the transmission mammography tube, or the thermal load to the X-ray tube, could therefore be reduced by more than an order of magnitude, from 5 kilowatts to approximately only 100 Watts. Such a reduction results not only a dramatic reduction of radiation dose to the breast tissue, but also a much simplified X-ray tube without the need to engage a rotational anode as well as a much smaller power supply to combine into an instrument at low cost.

More specifically, the phase-shifted imaging contrast requires spatial as well as temporal coherences. Assume a plane wave of an X-ray photon at wavelength λ traveling orthogonal to the said plane from the source to reach an object (the detector pixel) with a distance d. The spatial coherence requires that the differential emission points of the source layer, which is the effective thickness of the transmission target layer t, and it is not the e-beam focal area generating the Coolidge X-rays satisfy certain coherence conditions. The layer thickness it relates to a detector pixel size P as a spatial coherency or dispersion length.

P=λd/t≅3 μm for t~10 μm, d=50cm and λ(K of Ag)=1.24 μm/22,000

Next, the beam purity consideration, which is the temporal coherence length, or the energy dispersion size T. T can be considered as the wavelength λ being moderated by the line-emission photon energy E divided by its line-width ΔE in order to reach a full phase shift π.

T~λE/ΔE

With E/ΔE~104, T~0.3 μm with ΔE~4 eV, T is at an order of magnitude smaller than the spatial coherence length P. While spatial dispersion needs to be contained in each detector pixel, a full temporal coherence may not be necessary. A π phase shift gives rise to a contrast enhancement by three orders of magnitude from the radiographic imaging contrast of soft tissues, but an order of magnitude reduced phase shift in temporal contrast enhancement would still be highly useful. That is, using a photon beam of Ag target to penetrate the breast tissue with 50% transmission instead of the conventional mammography at 6% it could still provide sufficient image contrast, and reduce the tissue dose by an order of magnitude from this consideration alone.

Finally, evaluating the phase shift caused by a change of the index of refraction in the breast tissue. From the estimates considered above, there are 50,000 wavelengths in a spatial coherence length of 3 μm, or 5,000 wavelengths of a temporal coherence length of 0.3 μm, implying that the change of photon speed by one part in 50,000 or one part in 5,000 to gain a full π phase shift due to a change of the index of refraction (vacuum is 1 and water is 80) is relatively easy. Realistic image evaluations, however, must be experimentally evaluated from imaging the breast phantom which containing all the different items to be exposed as image.

Figure 4:
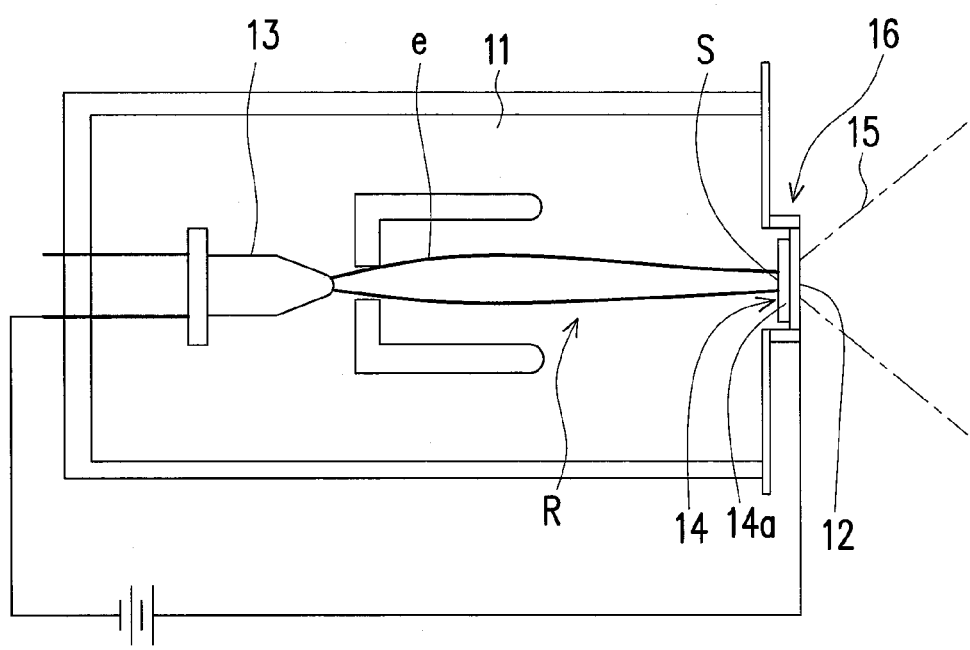
FIG. 4 is a schematic display of the transmission wide-angle X-ray tube according to one embodiment of this invention.

FIG. 4 is a schematic display of the transmission wide-angle X-ray tube as described in the embodiment of FIG. 1. The transmission X-ray tube 10 includes the casing 11, the anode 12, the transmission type target 14 and the cathode 13. The X-ray tube 10 is enclosed and sealed by the casing 11 and the casing 11 offers a vacuum environment within its enclosed internal space. The anode 12 is disposed within the end window 16 of the casing 11. The transmission type target 14 is disposed on the anode 12, and the transmission type target 14 includes at least a foil 14a (one foil 14a is shown in FIG. 3 as an example). The cathode 13 is disposed in the casing 11, suitable for emitting the electron beam e along a path R in the casing 11 to strike onto the target to generate the X-ray beam 15. Later, the X-ray beam 15 passes through the end window 16 and leaves the casing 11.

Furthermore, the electron beam e focuses on a small region, i.e. the area S, of the transmission type target 14 on the anode 12. The area S turns into the emission area of the X-ray beam 15. In this embodiment, the transmission X-ray tube 10 has relatively small emission area(s) of the X-ray beam 15, as small as 50 microns, for example.

Referring to FIGS. 2 & 4, the emission area of the X-ray beam 15 is the focal spots of the X-ray beam sources $S_A$, $S_B$. Smaller emission area may result in phase-shift contrast images of higher resolutions. Since the electron beam e of the transmission X-ray tube 10 is able to focus on the small area S to further provides X-ray beam sources $S_A$, $S_B$ of small focal area(s), high-resolution phase-shift contrast images can be acquired.

Figure 5:
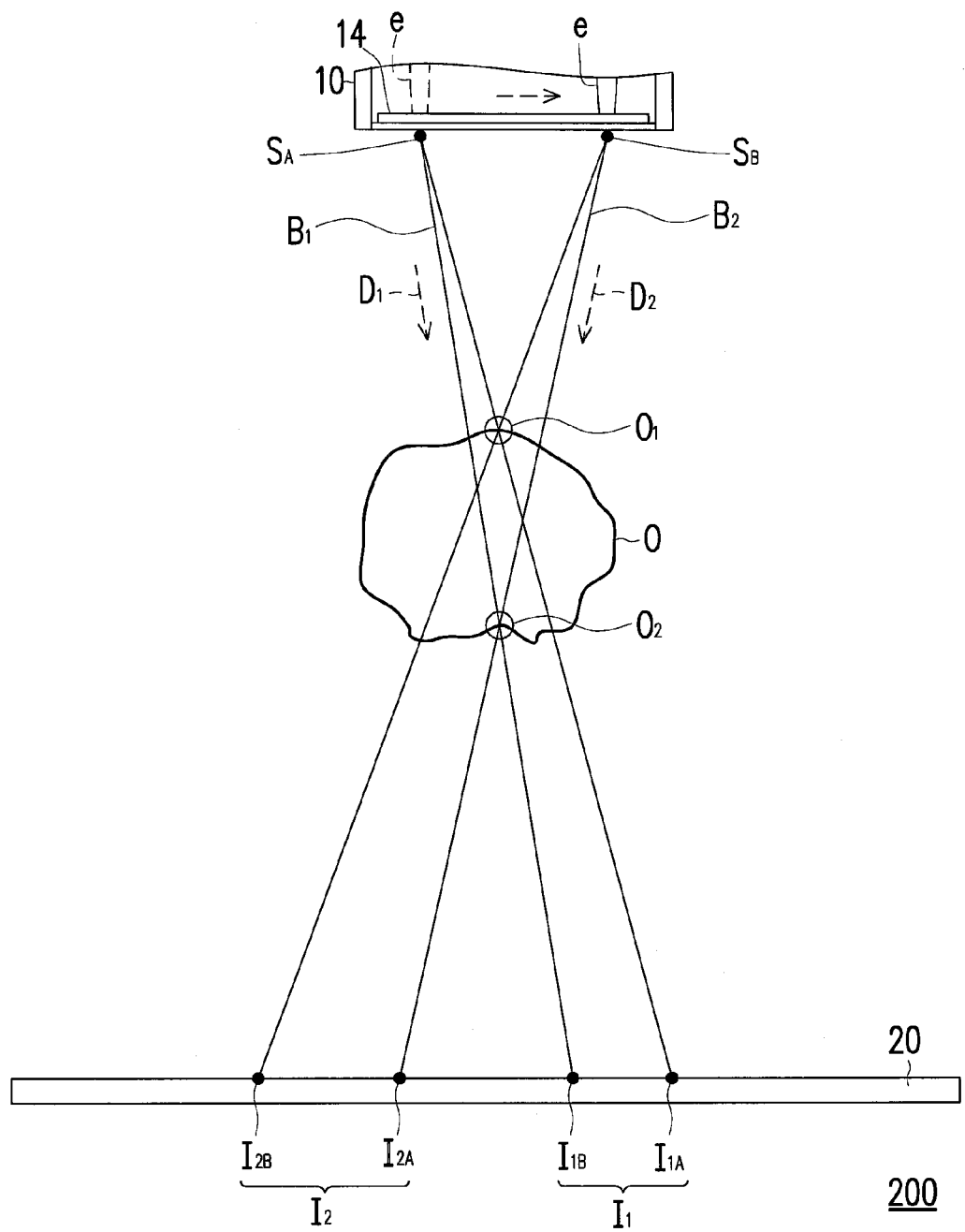
FIG. 5 is a schematic display of an X-ray phase-shift contrast imaging system for the X-ray phase-shift contrast imaging method according to one embodiment of this invention.
Figure 6:
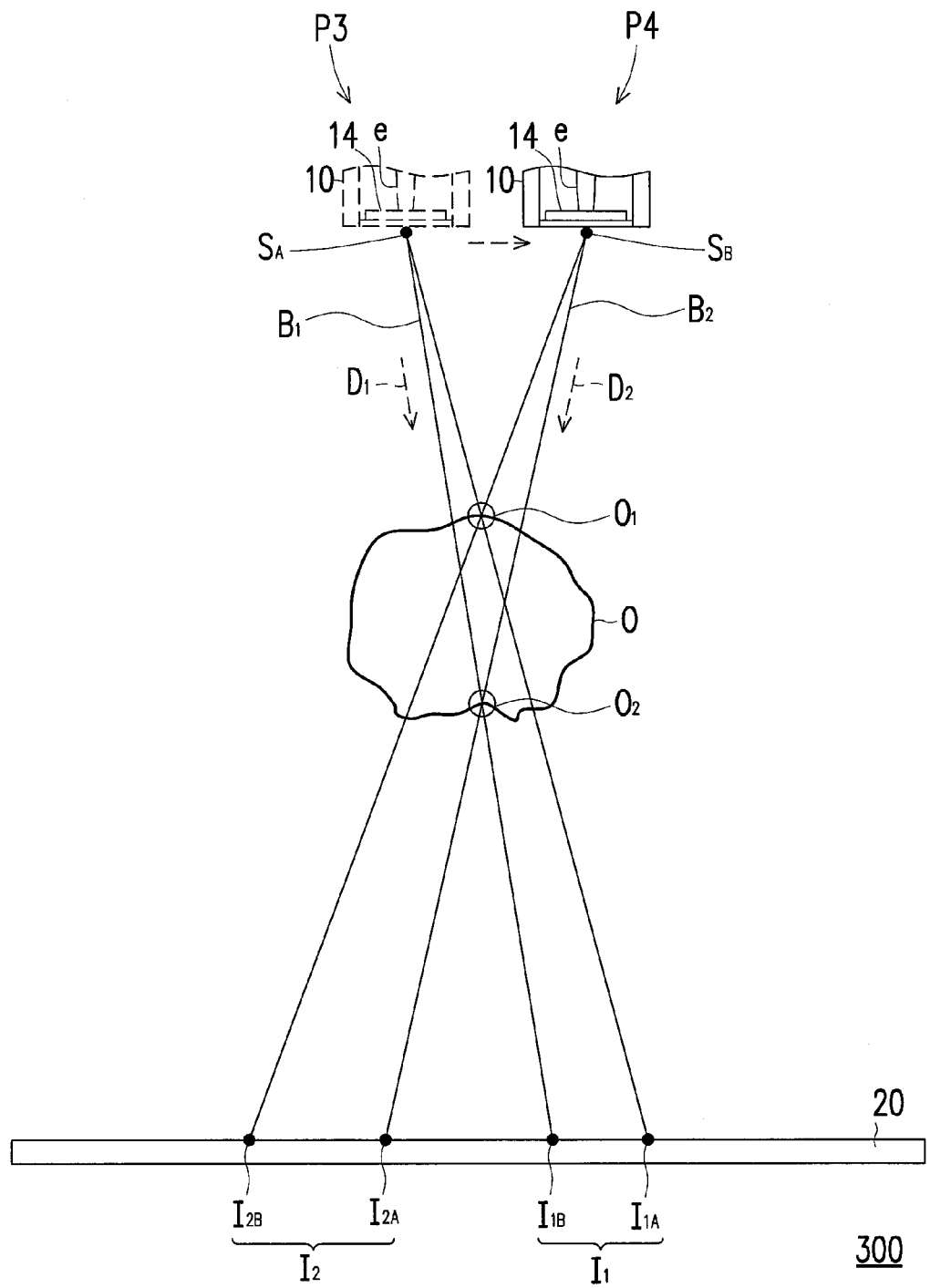
FIG. 6 is a schematic display of an X-ray phase-shift contrast imaging system for the X-ray phase-shift contrast imaging method according to another embodiment of this invention.

FIG. 5 is a schematic display of an X-ray phase-shift contrast imaging system for the X-ray phase-shift contrast imaging method according to one embodiment of this invention, while FIG. 6 is a schematic display of an X-ray phase-shift contrast imaging system for the X-ray phase-shift contrast imaging method according to another embodiment of this invention. For either one of the phase-contrast imaging systems, the single X-ray source at different positions is irradiated at the tissue to acquire the images. In FIG. 5, the X-ray phase-shift contrast imaging system 200 utilizes a transmission wide-angle X-ray tube 10. By way of the internal design of the transmission X-ray tube 10, the electron beam e strikes onto two positions of the transmission type target 14 to form X-ray beam sources $S_A$, $S_B$, which further provides X-ray beam $B_1$ irradiating at the tissue O in the first direction $D_1$ and X-ray beam $B_2$ irradiating at the tissue O in the second direction $D_2$.

Moreover, the X-ray beams $B_1$, $B_2$ can generate two adjacent X-ray images of different angles, i.e. the first X-ray image $I_1$ and the second X-ray image $I_2$, through any two target regions of the tissue O (such as the regions $O_1$ and $O_2$ in FIG. 5). Within the first X-ray image $I_1$, the pixels $I_{1A}$, $I_{1B}$ on the two-dimensional image detection array 20 are generated corresponding to the target region $O_1$ and $O_2$ of the tissue O. Within the second X-ray image $I_2$, the pixels $I_{2A}$, $I_{2B}$ on the two-dimensional image detection array 20 are generated corresponding to the target region $O_1$ and $O_2$ of the tissue O. In FIG. 6, the X-ray phase-shift contrast imaging system 300 also utilizes a transmission wide-angle X-ray tube 10, and the transmission X-ray tube 10, at two positions $P_3$, $P_4$, provides X-ray beam $B_1$ irradiating at the tissue O in the first direction $D_1$ and X-ray beam $B_2$ irradiating at the tissue O in the second direction $D_2$.

Figure 7:
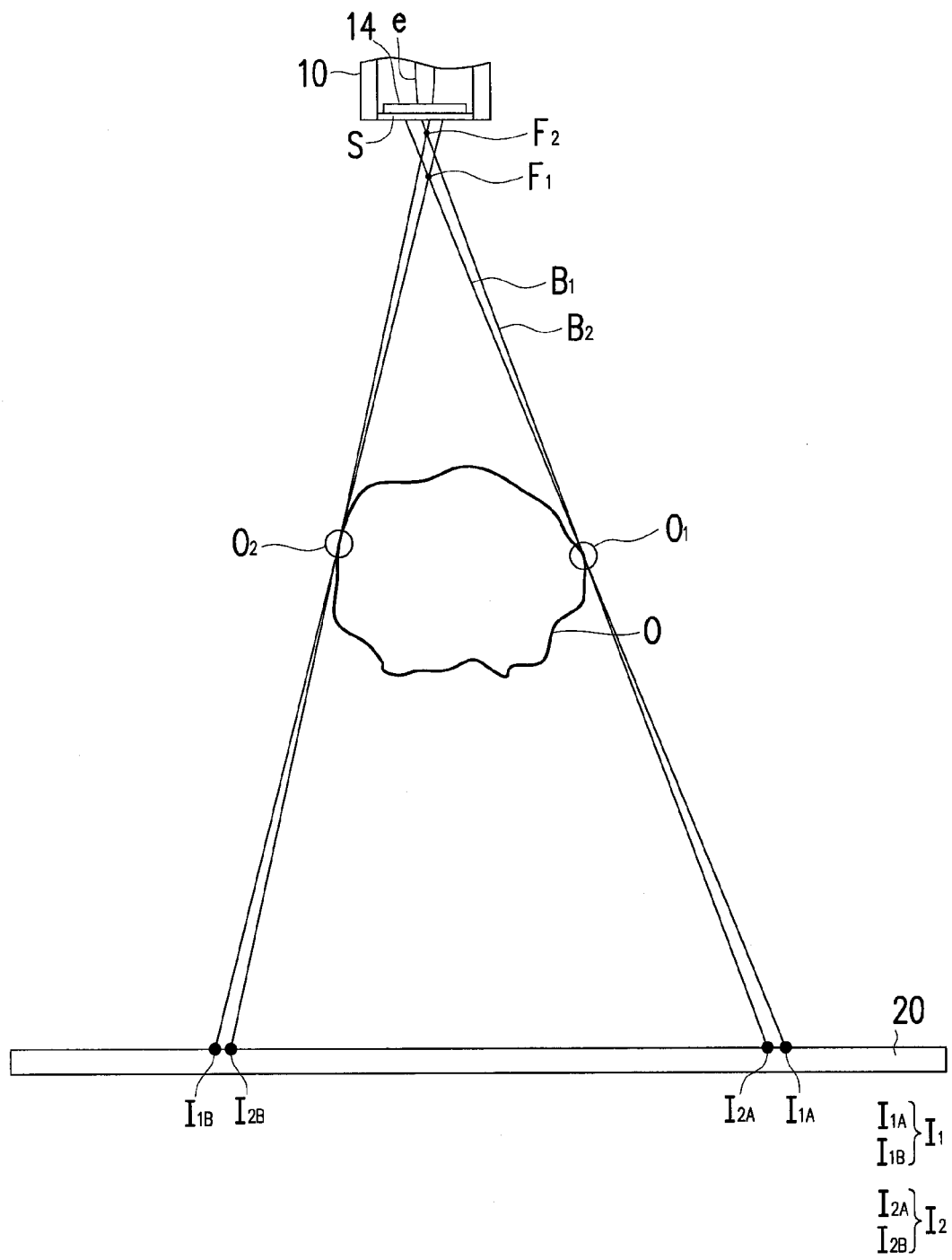
FIG. 7 is a schematic display of an X-ray phase-shift contrast imaging system for the X-ray phase-shift contrast imaging method according to another embodiment of this invention.

FIG. 7 is a schematic display of an X-ray phase-shift contrast imaging system for the X-ray phase-shift contrast imaging method according to another embodiment of this invention. Different to the phase-contrast imaging systems of FIGS. 2, 5 and 6, the phase-contrast imaging system of FIG. 7 utilizes the single X-ray source to generate X-ray beams with different focal spots beam, irradiating at the tissue to acquire the images. In FIG. 7, without changing the positions of the transmission X-ray tube 10, the single transmission wide-angle X-ray tube 10 of the X-ray phase-shift contrast imaging system 400 generates the X-ray beam $B_1$ of the first focus $F_1$ and the X-ray beam $B_2$ of the second focus $F_2$ by adjusting its focal lengths.

Moreover, the X-ray beams $B_1$, $B_2$ of different focal lengths can generate two adjacent X-ray images, i.e. the first X-ray image $I_1$ and the second X-ray image $I_2$, through any two target regions of the tissue O (such as the regions $O_1$ and $O_2$ in FIG. 7). Within the first X-ray image $I_1$, the pixels $I_{1A}$, $I_{1B}$ on the two-dimensional image detection array 20 are generated corresponding to the target region $O_1$ and $O_2$ of the tissue O. Within the second X-ray image $I_2$, the pixels $I_{2A}$, $I_{2B}$ on the two-dimensional image detection array 20 are generated corresponding to the target region $O_1$ and $O_2$ of the tissue O.

Therefore, following the procedures described in the embodiment of FIG. 2, the first X-ray image $I_1$ and the second X-ray image $I_2$ of the tissue O acquired by the phase-contrast imaging systems of FIGS. 5, 6 and 7 may be compared to define the voxels by converting the pixels into the voxels and the voxels are synthesized into a 3-D X-ray image. The details have been described before and will not be illustrated again thereafter.

Figure 8:
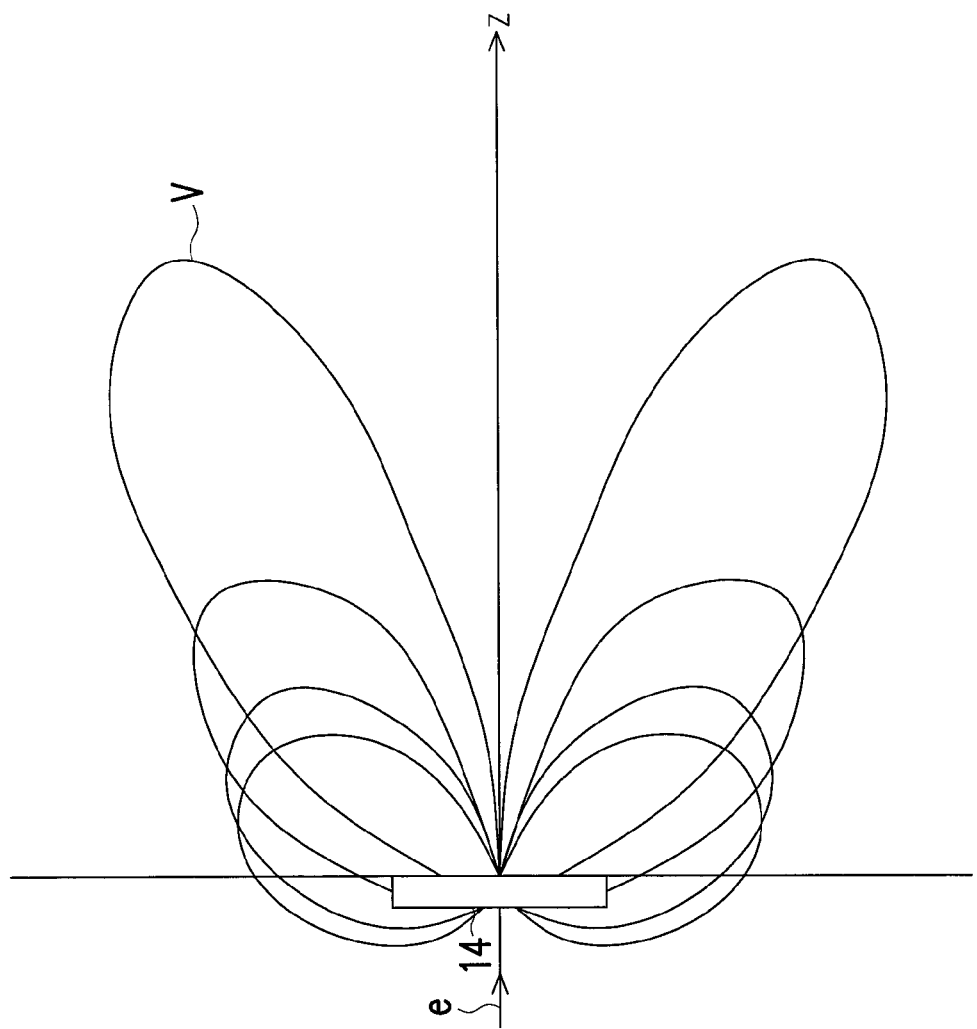
FIG. 8 illustrates the transform of the anode radiation generated from electrons hitting the target, in conjunction with the changes of the e-beam energy.

FIG. 8 illustrates the transform of the anode radiation generated from electrons hitting the target, in conjunction with the changes of the e-beam energy. Referring to FIGS. 6 and 8, when a bias of 100 Volts is applied to the transmission X-ray tube 10, electron speed is already 2% of the light speed. The typical e-beam of an X-ray tube at 100 keV has an electron speed approaching the light speed and is quite relativistic. The dipole radiation trajectories of the bremsstrahlung will transform from orthogonal to the e-beam to become parallel to the e-beam. The anode radiation trajectories of the bremsstrahlung generated by the transmission type target 14 will lean forward along the e-beam movement direction (direction Z in FIG. 8), like the trajectories V in FIG. 8. That is, the transmission X-ray tube 10 of FIG. 4 can generate conic wide-angle X-ray beams 15 through the transmission type target 14. Furthermore, the X-ray beam 15 can directly emits from the other side of the transmission type target 14, so that the whole conic wide-angle X-ray beam 15 may be completely used for phase-contrast imaging. For example, the transmission X-ray tube 10 of FIG. 4 can generate conic wide-angle X-ray beams 15 having an azimuth angle of 160 degrees or more.

Because the transmission wide-angle X-ray tube 10 is able to generate conic X-ray beams 15 of large angles, the irradiation reach of X-ray is increased, the distance between the emission point and the object is reduced and the magnification factor is larger. Hence, for the X-ray phase-shift contrast imaging method of FIG. 1, the efficiency of the X-ray beams $B_1$, $B_2$ for acquiring the first X-ray image $I_1$ and the second X-ray image $I_2$ is enhanced, further lowering the costs of the X-ray phase-shift contrast imaging method.

Figure 9:
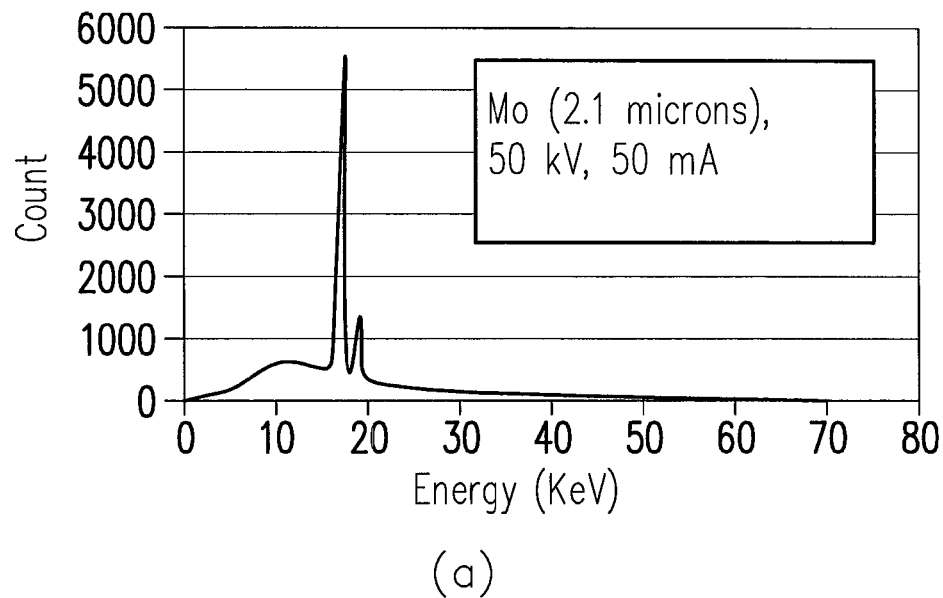
FIG. 9(a)-(b) are photon spectra of X-ray beams generated by the transmission wide-angle X-ray tube.
Figure 9:
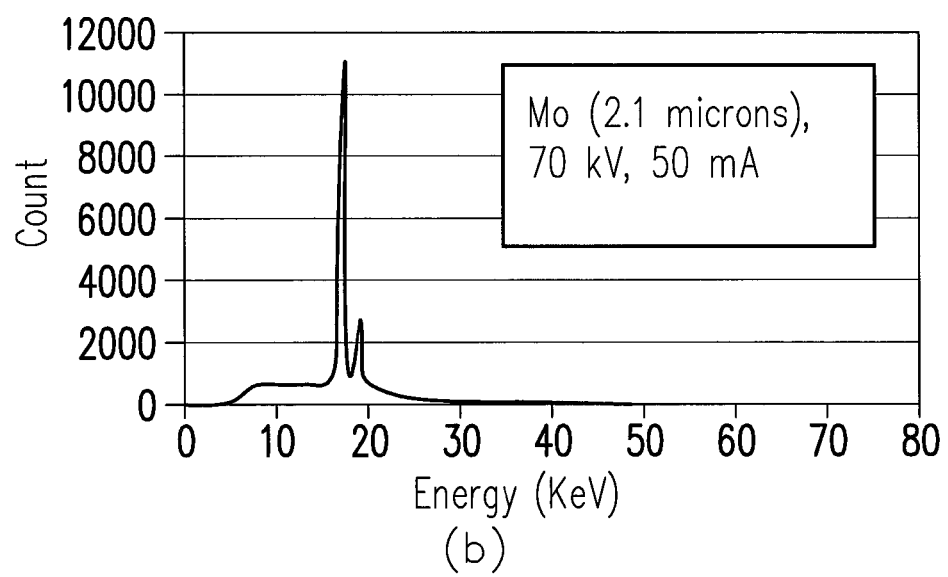
Figure 10:
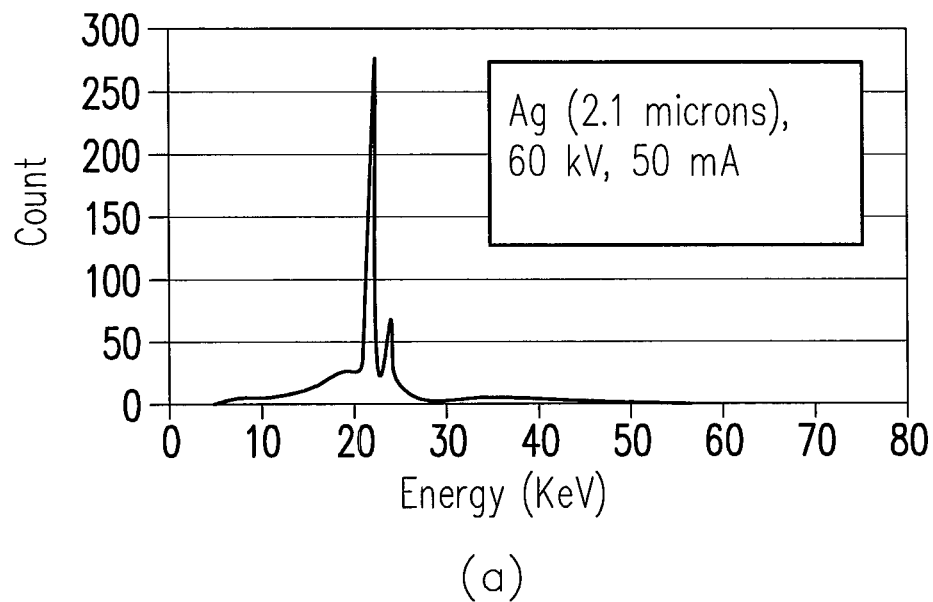
FIG. 10(a)-(b) are photon spectra of X-ray beams generated by the transmission wide-angle X-ray tube.
Figure 10:
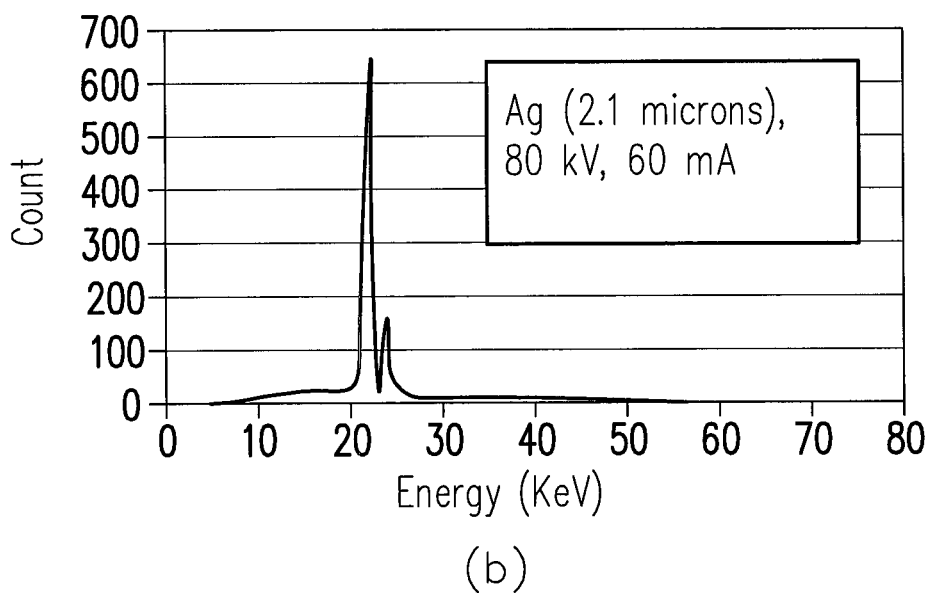

FIG. 9 and FIG. 10 are photon spectra of X-ray beams generated by the transmission wide-angle X-ray tube. Referring to FIGS. 4, 9 and 10, taking the breast tissue as an example, for the transmission X-ray tube 10, the material of the transmission type target 14 may be silver (Ag), molybdenum (Mo) or cadmium (Cd), for example. FIGS. 9(a) and 9(b), for the transmission type target consisting of Mo, show the photon spectra of wide-angle X-ray beams generated by the transmission X-ray tube with the electron beams of different energy. FIGS. 10(a) and 10(b), for the transmission type target consisting of Ag, show the fluorescent photon spectra of wide-angle X-ray beams generated by the transmission X-ray tube with the electron beams of different energy.

The X-ray beam 15 generated by the transmission X-ray tube 10 includes relatively high throughput characteristic line emissions and relatively low throughput bremsstrahlung (brem), both have the primary radiation generated from electron hitting the target layer and the fluorescent radiation from the target surface layer by absorbing the prior brem radiation. The throughput ratio of the characteristic line emissions and the level is at least 5:1. The energy of the electron beam e in the transmission X-ray tube 10 is more than twice of the energy of the characteristic X-ray. The thickness of the transmission type target 14 is at least 2.1 microns. In addition, the thickness of the transmission type target 14 is larger than the penetration depth of the electron beam e into the transmission type target 14, preferably t is about two times of the depth.

It is noted that the characteristic X-rays are the line emissions of the specific energies just below its absorption edge and are generated from the electrons striking the target atoms. These photons could easily penetrate the target material with minimal absorption. The brem (also called continuous X-rays) photons are X-rays of continuous spectrum, usually hindered by the target. Therefore, the transmission type target 14 itself absorbs the high energy beams to fluorescent characteristic line emissions, and in the process \, filtering out a major portion of the low energy beam 15, while converting the high energy brem into fluorescence and thereby increasing the characteristic X-rays while reducing continuous X-rays. The transmission type target 14 would increase the ratio of the characteristic line X-rays in the X-ray spectrum, that is, generate monochromatic line-emissions of high brightness without shifting the photon spectrum. For phase-shift contrast imaging, it is important to have highly coherent line-emissions whose line width is only a few eV in order to create a realistic spatial coherence length that can be covered by a detector pixel, as considered before. By improving the phase shift interference for imaging contrast, it simplifies X-ray imaging in general and the mammogram in particular.

Referring back to FIGS. 9 and 10, in the embodiment of FIG. 9, the transmission type target 14 is made of Mo with a thickness of 2.1 microns. In the embodiment of FIG. 10, the transmission type target 14 is made of silver with a thickness of 41 microns. From FIGS. 9 and 10, as the voltage of the transmission wide-angle X-ray tube 10 is increased, the positions (photon energy) of the characteristic X-rays in the photon spectrum of the X-ray beam remain fixed, but the intensities of the characteristic X-ray lines are increased. In details, certain X-ray tubes may use additional filtering elements to filter out the continuum X-rays, but they also lower the intensities of the characteristic line-emissions. However, for the transmission X-ray tube 10, it is possible to increase the voltage applied to the X-ray tube to increase the characteristic line emissions in the photon spectrum, and obtain a higher ratios of the characteristic lines.

On the other hand, if the X-ray beams $B_1$, $B_2$ are monochromatic in FIG. 2, the impacts of the continuum X-rays to the tissue O can be reduced and the absorbed radiation dose (skin dose) of the tissue O can be lowered. Furthermore, if the tissue O is a soft tissue, the X-ray beams $B_1$, $B_2$ of higher energy have relatively deeper penetration and relatively lower absorbed radiation amount. That is, higher energy X-ray beams $B_1$, $B_2$ can reduce the linear energy transfer (LET) of the tissue O, thus reducing the absorbed radiation dose of the tissue O from the X-ray beams $B_1$, $B_2$. By choosing the material of the transmission type target 14, the transmission X-ray tube 10 of FIG. 4 can generate monochromatic, high energy and wide-angle X-ray beam 15, so that the absorbed radiation dose of the tissue O can be greatly reduced for the X-ray phase-shift contrast imaging systems 100, 200, 300 as shown in FIGS. 2, 5 and 6.

Generally, for obtaining the images from the differences in the absorption amounts of X-ray, the soft tissues (such as the breasts) have to be continually compressed so that the X-rays can penetrate the soft tissues of the same thickness and transmit the same to the detector. In the embodiment of FIG. 1, the X-ray phase-shift contrast imaging method employs the transmission X-ray tube (such as the transmission wide-angle X-ray tube 10 in FIG. 4) for phase-shift contrast imaging, so that the compression of the soft tissues during X-ray phase-contrast imaging may be avoided.

In summary, for the X-ray phase-shift contrast imaging method and the X-ray phase-shift contrast imaging system, the transmission wide-angle X-ray tube generates high brightness characteristics X-rays and the generated X-ray beams are irradiated to the tissue respectively in the first and second directions to form the first and second X-ray images. By doing so, the 3-D X-ray images may be easily obtained and the X-ray dose to the tissue may be lowered as well.

The X-ray phase-shift contrast imaging method of this invention utilizes characteristic X-rays of high throughput irradiating at the target from different positions or with different focal positions so as to form different X-ray images. The X-ray images are compared to define the voxels and combined to obtain the 3-D X-ray image. By using X-ray phase-shift contrast for imaging the soft tissue, the level of the image contrast may be enhanced several orders of magnitude and the linear energy transfer of the high energy photon beam is greatly reduced. Hence, the radiation dose imparted to the tissue may be greatly reduced.

Also, by employing at least one or two transmission X-ray tubes, a novel dual cone beam CT algorithm may be applied. Two views may be conducted with electronic switching and two sequential images with high resolution may be delivered, without the needs of compressing the breasts.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An X-ray phase-shift contrast imaging method, comprising:
   providing at least an X-ray tube;
   generating an X-ray beam by the at least X-ray tube, wherein the X-ray beam irradiates to a tissue in a first direction to obtain a first X-ray image and in a second direction to obtain a second X-ray image, and the X-ray beam has a throughput ratio of characteristic X-rays and continuum X-rays is at least 5:1 and the X-ray beam has an azimuth angle of 160 degrees; and receiving and comparing the first X-ray image and the second X-ray image sequentially by a two-dimensional image detection array to define voxels, so as to obtain a three-dimensional X-ray image.

2. The X-ray phase-shift contrast imaging method of claim 1, wherein the at least X-ray tube comprises:
a casing, offering a vacuum environment;
an anode, disposed within an end window of the casing;
a transmission type target, disposed on the anode, wherein the transmission type target includes at least a foil; and
a cathode, disposed in the casing, wherein the cathode is suitable for emitting an electron beam along a path in the casing to strike onto the transmission type target to generate the X-ray beam transmitting through the end window.

3. The X-ray phase-shift contrast imaging method of claim 1, wherein the tissue is a soft tissue.

4. The X-ray phase-shift contrast imaging method of claim 1, wherein a material of a transmission type target comprises Molybdenum (Mo), silver (Ag) or Cadmium (Cd).

5. The X-ray phase-shift contrast imaging method of claim 1, wherein the X-ray beam is a wide-angle conic X-ray beam.

6. The X-ray phase-shift contrast imaging method of claim 1, wherein the characteristic X-rays are monochromatic X-rays.

7. The X-ray phase-shift contrast imaging method of claim 1, wherein the tissue is a breast tissue.

8. An X-ray phase-shift contrast imaging system, suitable for obtaining images of a tissue, comprising:
a two-dimensional image detection array; and
two X-ray tubes respectively located at a first position and a second position, wherein the two X-ray tubes generate X-ray beams sequentially irradiating on the tissue respectively in a first direction to form a first X-ray image and in a second direction to form a second X-ray image, wherein the first X-ray image and the second X-ray image are received by the two-dimensional image detection array, wherein each of the two X-ray tubes includes a transmission type target located on an anode and a cathode emitting an electron beam to bombard the transmission type target so as to generate the X-ray beams, the X-ray beam has a throughput ratio of characteristic X-rays and continuum X-rays is at least 5:1 and the X-ray beam has an azimuth angle of 160 degrees.

9. The X-ray phase-shift contrast imaging system of claim 8, wherein an energy of the electron beam is more than twice of the energy of the characteristic X-ray and a thickness of the transmission type target is at least 2.1 microns.

10. The X-ray phase-shift contrast imaging system of claim 8, wherein a thickness of the transmission type target is larger than a penetration depth of the electron beam into the transmission type target.

11. The X-ray phase-shift contrast imaging system of claim 8, wherein a material of the transmission type target comprises molybdenum (Mo), silver (Ag) or Cadmium (Cd).

12. The X-ray phase-shift contrast imaging system of claim 8, wherein the X-ray beam is a wide-angle conic X-ray beam.

13. The X-ray phase-shift contrast imaging system of claim 8, wherein the characteristic X-rays are monochromatic X-rays.

14. An X-ray phase-shift contrast imaging system, suitable for obtaining images of a tissue, comprising:
a two-dimensional image detection array; and
a transmission X-ray tube, for generating an X-ray beam, wherein the X-ray beam is generated by the transmission X-ray tube located respectively at a first position and a second position to irradiate on the tissue sequentially in a first direction to form a first X-ray image and in a second direction to form a second X-ray image, wherein the first X-ray image and the second X-ray image are received by the two-dimensional image detection array,
wherein the transmission X-ray tube includes a transmission type target located on an anode and a cathode emitting an electron beam to bombard the transmission type target so as to generate the X-ray beams, the X-ray beam has a throughput ratio of characteristic X-rays and continuous X-rays is at least 5:1 and the X-ray beam has an azimuth angle of 160 degrees.

15. The X-ray phase-shift contrast imaging system of claim 14, wherein an energy of the electron beam is more than twice of the energy of the characteristic X-ray and a thickness of the transmission type target is at least 2.1 microns.

16. The X-ray phase-shift contrast imaging system of claim 14, wherein a thickness of the transmission type target is larger than a penetration depth of the electron beam into the transmission type target.

17. The X-ray phase-shift contrast imaging system of claim 14, wherein a material of the transmission type target comprises Molybdenum (Mo), silver (Ag) or Cadmium (Cd).

18. The X-ray phase-shift contrast imaging system of claim 14, wherein the X-ray beam is a wide-angle conic X-ray beam.

19. The X-ray phase-shift contrast imaging system of claim 14, wherein the characteristic X-rays are monochromatic X-rays.

20. An X-ray phase-shift contrast imaging method, comprising:
providing at least an X-ray tube;
generating a first X-ray beam and a second X-ray beam by the at least X-ray tube, wherein the first and second X-ray beams are of different focuses and the first X-ray beam irradiates to a tissue in a first direction to obtain a first X-ray image and the second X-ray beam irradiates to the tissue in a second direction to obtain a second X-ray image, and either of the first and second X-ray beams has a throughput ratio of characteristic X-rays and continuous X-rays is at least 5:1 and has an azimuth angle of 160 degrees; and
receiving and comparing the first X-ray image and the second X-ray image by a two-dimensional image detection array to define voxels, so as to obtain a three-dimensional X-ray image.

* * * * *